US00PP21408P2

(12) United States Plant Patent
O'Connell

(10) Patent No.: US PP21,408 P2
(45) Date of Patent: Oct. 19, 2010

(54) ***ALOE* PLANT NAMED 'BLIZZARD'**
(50) Latin Name: ***Aloe* hybrid**
Varietal Denomination: Blizzard

(76) Inventor: Renee O'Connell, 1801 Tierra Libertia, Escondido, CA (US) 92026

( * ) Notice: Subject to any disclaimer, the term of this patent is extended or adjusted under 35 U.S.C. 154(b) by 0 days.

(21) Appl. No.: 12/455,723

(22) Filed: Jun. 6, 2009

(51) Int. Cl.
*A01H 5/00* (2006.01)

(52) U.S. Cl. ..... Plt./373
(58) Field of Classification Search ..... Plt./373
See application file for complete search history.

*Primary Examiner*—Annette H Para

(57) ABSTRACT

A new and distinct *Aloe* cultivar named 'Blizzard' is disclosed, characterized a very compact, upright plant habit, strong foliage with bright white variegation, and frequent flowering periods. Plants freely produce offsets. The new variety is an *Aloe*, typically produced as a garden or container plant.

1 Drawing Sheet

Figure 1:
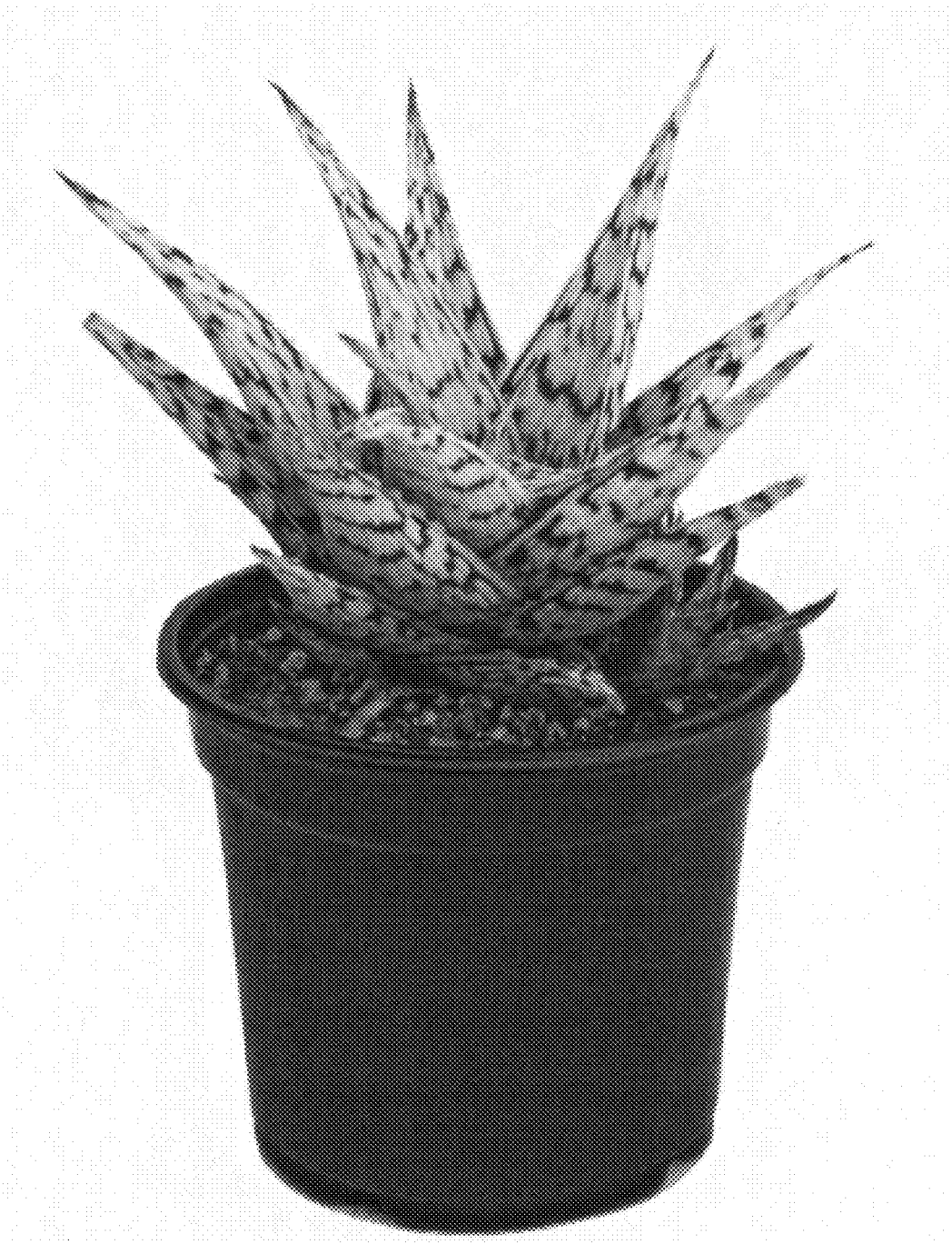

Latin name of the genus and species: *Aloe* hybrid.
Variety denomination: 'Blizzard'.

BACKGROUND OF THE INVENTION

The new cultivar is a product of a planned breeding program. The new variety originated from a cross pollination of the seed parent, *Aloe* 'Doran Black' unpatented with the pollen parent an unpatented proprietary *Aloe* hybrid referred to as '#51.' The crossing was made in during April of 2006 in Vista, Calif., at a commercial greenhouse. 'Blizzard' was discovered by the inventor, Renee O'Connell, in July 2007, in Vista, Calif. at a commercial greenhouse.

Asexual reproduction of the new cultivar 'Blizzard' was first performed in Vista, Calif., at a commercial greenhouse by vegetative leaf cuttings in July 2007. 'Blizzard' has since produced several generations and has shown that the unique features of this cultivar are stable and reproduced true to type.

SUMMARY OF THE INVENTION

The cultivar 'Blizzard' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Blizzard.' These characteristics in combination distinguish 'Blizzard' as a new and distinct *Aloe* cultivar:

1. Upright plant morphology.
2. Bright white foliage variegation.
3. Frequent blooming periods.
4. Small plant size.
5. Free offset production.

PARENTAL COMPARISON

Plants of the new cultivar 'Blizzard' are similar to the seed parent 'Doran Black' in most horticultural characteristics. However, 'Blizzard' is more upright, with brighter white foliage variegation. Additionally, in commercial shipping and growing situations, 'Blizzard' has foliage that resists breaking better than 'Doran Black'.

Plants of the new cultivar 'Blizzard' are similar to the pollen parent '#51' in most horticultural characteristics.

However, 'Blizzard' is a much more upright plant form, with brighter white foliage variegation, and also more white coloration on the foliage. Additionally, in commercial shipping and growing situations, 'Blizzard' has foliage that resists breaking better than '#51.'

COMMERCIAL COMPARISON

'Blizzard' can be compared to the unpatented commercial variety *Aloe* 'Dapple Green.' Plants of *Aloe* 'Dapple Green' are similar to plants of 'Blizzard' in most horticultural characteristics, however, 'Blizzard' is a much more upright plant form, with brighter white foliage variegation. Additionally, in commercial shipping and growing situations, 'Blizzard' has foliage that resists breaking better.

'Blizzard' can also be compared to the unpatented commercial variety *Aloe* 'Lizard Lips.' Plants of *Aloe* 'Lizard Lips' are similar to plants of 'Blizzard' in most horticultural characteristics, however, 'Blizzard' is a much more upright plant form, with brighter white foliage variegation. Additionally, in commercial shipping and growing situations, 'Blizzard' has foliage that resists breaking better. 'Blizzard' also produces more flowers than 'Lizard Lips'.

BRIEF DESCRIPTION OF THE PHOTOGRAPH

The accompanying photograph in FIG. 1 illustrates in full color a typical plant of 'Blizzard' grown outdoors in Vista, Calif. This plant is approximately 7 months old, shown in a 4 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Pantone Process Color System Guide, except where general terms of ordinary dictionary significance are used. The following observations and measurements describe 'Blizzard' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'Blizzard'.
Age of the plant described: Approximately 6.5 months.

PROPAGATION

Time to initiate roots: Approximately 20 to 25 days at 21° C.
Root description: Fibrous.
Propagation method: Vegetative divisions.

PLANT

Growth habit: Compact, rosulate succulent.
Container size: 4 inch.
Height: Approximately 5 cm to top of highest leaf. Approximately 43 cm to top of highest inflorescence.
Plant spread: Approximately 15 cm.
Growth rate: Slow.
Branching characteristics: Rosulate plant producing offsets.

FOLIAGE

Leaf:
*Arrangement.*—Rosulate.
*Average length.*—Approximately 9 cm.
*Widest width.*—Approximately 3.25 cm.
*Width at base.*—2.25 cm.
*Shape of blade.*—Deltoid lanceolate.
*Apex.*—Acute.
*Base.*—Rounded.
*Margin.*—Undulate, somewhat serrate, with unevenly dispersed cartilaginous serrulate teeth.
*Texture of top surface.*—Medium coarse with raised ridges at intervals.
*Texture of bottom surface.*—Less coarse than upper surface with raised ridges.
*Quantity of leaves per plant.*—Approximately 14.
*Color.*—Young foliage upper side: Near 273.5 background color; color of lighter raised areas S 40-8 Pantone, near tip near S 308-1. Young foliage under side: Near 273.5 background color; color of lighter raised areas S 40-8 Pantone, near tip near S 308-1. Mature foliage upper side: Near S 311-9 Pantone; toward tip of leaf near S 317-1 Pantone; near S 308-1 to S 308-2 Pantone near stem attachment. Mature foliage under side: Near S 317-1 Pantone, toward tip of leaf near S 317-1 Pantone.
*Venation.*—Type: Parallel Venation color upper side: Near 70-7 Pantone Venation color under side: Near 70.9 Pantone

FLOWER

Natural flowering season: Various times of year; more frequently during late winter-spring.
Inflorescence type and habit: Heterothetic raceme.
Flower longevity on plant: 2-3 days.
Quantity of flowers: Approximately 27.
Total inflorescence size:
*Height.*—Approximately 44.5 cm.
*Width.*—Approximately 0.375 cm.
Corolla:
*Arrangement.*—Arranged in two whorls of 3 petals.
*Size.*—Length: Approximately 1.82 cm. Width: Approximately 0.62 cm at widest point and 0.38 cm at narrowest point. Lobe Length: Approximately 1.78 cm. Lobe Width: 0.4 cm. at widest.
*Margin.*—Entire.
*Shape.*—Oblong.
*Apex.*—Acute.
*Texture.*—Smooth.
Color:
*Petals.*—When opening: Outer surface: Near 97.2 Pantone, superior margin 97.6, tip S315-1 to s 315-2 Pantone. Inner surface: Near 97.2 Pantone; 97.2 to 97-4 at base. Fully opened: Outer surface: Near S 97-2 Pantone. Inner surface: Near S 97-2 Pantone. Midrib color: S 97-4 and ends between S 315-1 and S 315-2 Pantone. Color Changes when Aging: Near S 98-2 Pantone, all surfaces.
Bud:
*Shape.*—Oblong.
*Length.*—Approximately 1.6 cm.
*Diameter.*—Approximately 0.4 cm. at widest.
*Color.*—Near S 92-2 Pantone; S 98-4 at tip of bud; S 42-2 green midstripe.
*Sepals.*—No true sepals.
Pedicels:
*Length.*—Approximately 1.54 cm; varying to 0.95 near tip.
*Width.*—Approximately 0.006 cm.
*Aspect.*—Slanted.
*Color.*—Near S 97-2 Pantone.
Scape:
*Length.*—Approximately 44 cm.
*Width.*—Approximately 0.3 cm at base and 0.1 at apex
*Strength.*—Moderately strong.
*Color.*—Near S 74-3 to S 74-4 Pantone.
Fragrance: None.

REPRODUCTIVE ORGANS

Stamens:
*Number.*—Average 6.
*Filament length.*—Approximately 1.43 to 1.46 cm.
*Filament color.*—Near S 97-8 Pantone at base; near S 46-5 Pantone at tip.
*Anther length.*—Varies from 0.18 to 0.22 cm.
*Anther color.*—Near S 52-1 Pantone.
*Anther shape.*—Elliptical long.
*Pollen.*—Near S 2-4 Pantone.
Pistil:
*Number.*—1.
*Length.*—Approximately 1.27 cm.
*Style color.*—Near S 26-3 Pantone.
*Stigma.*—Shape: Circular. Color: Near S 26-3 Pantone. Ovary color: Near S 28-3 Pantone.

OTHER CHARACTERISTICS

Seeds and fruits: Fruit is oblong; 0.8 cm diameter, 3 carpels.
Temperature tolerance: Tolerates temperatures from approximately −2 C to 32 C.
Disease/pest resistance: Neither resistance nor susceptibility to normal diseases and pests of *Aloe* has been observed.
Drought tolerance: Tolerates at least 2 weeks of high temperatures without supplemental water, showing no serious damage to plant.

What is claimed is:

1. A new and distinct cultivar of *Aloe* plant named 'Blizzard' as herein illustrated and described.

* * * * *